US012685517B2

(12) United States Patent
Maccio et al.

(10) Patent No.: US 12,685,517 B2
(45) Date of Patent: Jul. 21, 2026

(54) DEMATERIALIZED, MULTI-USER SYSTEM FOR THE ACQUISITION, GENERATION AND PROCESSING OF ULTRASOUND IMAGES

(71) Applicant: Esaote S.p.A., Genoa (IT)

(72) Inventors: Marco Maccio, Genoa (IT); Luca Russano, Genoa (IT)

(73) Assignee: Esaote S.p.A., Genoa (IT)

( * ) Notice: Subject to any disclaimer, the term of this patent is extended or adjusted under 35 U.S.C. 154(b) by 941 days.

(21) Appl. No.: 17/742,041

(22) Filed: May 11, 2022

(65) Prior Publication Data

US 2022/0361854 A1    Nov. 17, 2022

(30) Foreign Application Priority Data

May 13, 2021    (IT) ........................ 102021000012350

(51) Int. Cl.
*A61B 8/00*            (2006.01)

(52) U.S. Cl.
CPC .............. *A61B 8/565* (2013.01); *A61B 8/464* (2013.01)

(58) Field of Classification Search
None
See application file for complete search history.

(56) References Cited

U.S. PATENT DOCUMENTS

| | | | |
|---|---|---|---|
| 2004/0015079 A1* | 1/2004 | Berger | ................... G01S 7/5208 600/443 |
| 2005/0265267 A1 | 12/2005 | Hwang | |
| 2011/0169933 A1* | 7/2011 | Touboul | ............... A61B 5/0022 348/207.1 |
| 2011/0191822 A1* | 8/2011 | Pinsky | .................... G06F 15/16 726/3 |
| 2015/0313578 A1* | 11/2015 | Yu | ......................... A61B 8/4254 600/459 |
| 2017/0105701 A1 | 4/2017 | Pelissier et al. | |
| 2019/0117190 A1* | 4/2019 | Djajadiningrat | ...... G06T 19/006 |
| 2019/0247010 A1* | 8/2019 | Barnacka | ................. A61B 8/02 |
| 2021/0000407 A1* | 1/2021 | Firouzi | ............... A61B 8/0808 |

OTHER PUBLICATIONS

Italian Search Report and Written Opinion dated Jan. 27, 2022, which issued in the corresponding Italian Patent Application No. IT 202100012350.

* cited by examiner

*Primary Examiner* — Michael J Carey
*Assistant Examiner* — Marjan Saboktakin
(74) *Attorney, Agent, or Firm* — Dickinson Wright PLLC

(57) ABSTRACT

In a dematerialized ultrasound system, i.e. comprising a probe for transmitting and receiving ultrasound signals and a generic processing hardware made of one or more distributed processing units, the functions relating to the processing steps for the generation and processing of the images are in the form of software programs that encode instructions for the aforementioned generic hardware which make it capable of executing said processing steps. In order to make the computational and data interchange burden less heavy between the units of the distributed architecture of the system and to make the distribution of processing steps more flexible between one or more of the components of the distributed system, the programs are created under form of applications included in containers managed by a container management engine.

14 Claims, 6 Drawing Sheets

360

APP 1 370  APP 2 370  APP n 370
380 Bins/Libs  380 Bins/Libs  380 Bins/Libs
CONTAINER ENGINE  340
OPERATING SYSTEM  330
PROCESSOR HARDWARE  320
NON GENERIC DEDICATED HARDWARE COMPONENTS  310

300

360

APP 1 370

APP 2 370

APP n 370

380 Bins/Libs

380 Bins/Libs

380 Bins/Libs

CONTAINER ENGINE 340

OPERATING SYSTEM 330

PROCESSOR HARDWARE

320

NON GENERIC DEDICATED HARDWARE COMPONENTS 310

300

| PROBE 101 | LOCAL PROCESSING UNIT 240 | CENTRAL PROCESSING UNIT 200 | DISPLAY AND USER INTERFACE 230, 250 |
|---|---|---|---|
| Transmission and reception | D/A to TX and A/D to RX conversion | Beamforming in TX and RX Images Formation Back-end processing Further processing | Visualization Command input |
| Transmission and reception | conversion D/A to TX and A/D to RX Beamforming to TX and RX | Images Formation Back-end processing Further processing | Visualization Command input |
| Transmission and reception | conversion D/A to TX and A/D to RX Beamforming to TX and RX Images Formation Back-end processing | Further processing | Visualization Command input |
| Transmission and reception D/A to TX and A/D to RX conversion | Beamforming in TX and RX Images Formation Back-end processing | Further processing | Visualization Command input |
| Transmission and reception D/A to TX and A/D to RX conversion Beamforming in TX and RX | Images Formation Back-end processing | Further processing | Visualization Command input |
| Transmission and reception D/A to TX and A/D to RX conversion Partial Beamforming in TX and RX | Partial Beamforming in TX and RX Images Formation Back-end processing | Further processing | Visualization Command input |
| Transmission and reception Beamforming in TX | conversion A/D in RX Beamforming in RX Images Formation Back-end processing | Images Formation Back-end processing Further processing | Visualization Command input |
| Transmission and reception Beamforming in TX Beamforming in analogue partial RX | conversion A/D in RX Partial beamforming in RX Images Formation Back-end processing | Images Formation Back-end processing Further processing | Visualization Command input |

Fig. 4A

| PROBE 101 | CENTRAL PROCESSING UNIT 200 | DISPLAY AND USER INTERFACE 230, 250 |
|---|---|---|
| Transmission and reception conversion D/A in TX e A/D in RX Beamforming in TX and in RX Images Formation Back-end processing | Further processing | Visualization Command input |
| Transmission and reception conversion D/A in TX and A/D in RX | Beamforming in TX and in RX Images Formation Back-end processing Further processing | Visualization Command input |
| Transmission and reception conversion D/A in TX and A/D in RX Beamforming in TX and in RX | Images Formation Back-end processing Further processing | Visualization Command input |
| Transmission and reception conversion D/A in TX and A/D in RX Partial Beamforming in TX and RX | Beamforming parzial in TX and in RX Image Formation Back-end processing Further processing | Visualization Command input |
| Transmission and reception Beamforming in TX | conversion A/D in RX Beamforming in RX Images Formation Back-end processing Further processing | Visualization Command input |
| Transmission and reception Beamforming in TX Beamforming in analogue partial RX | conversion A/D in RX Partial beamforming in RX Images Formation Back-end processing Further processing | Visualization Command input |

Fig. 4B

DEMATERIALIZED, MULTI-USER SYSTEM FOR THE ACQUISITION, GENERATION AND PROCESSING OF ULTRASOUND IMAGES

BACKGROUND

Field

The present disclosure relates generally to a multi-user system for the acquisition, generation and processing of ultrasound images.

Description of Related Art

Typically, the processing steps of the reception signals obtained by the ultrasound probes, i.e. the electrical signals generated by the electroacoustic transducers of the set of transducers provided on each probe, following the capture of the echoes of reflection of the ultrasonic pulses transmitted to an object in examination, include the following processes:

calculation of transmission timing, generation of digital transmission signals, D/A (digital/analogue) conversion of transmission signals, A/D (analogue/digital) conversion of received signals, beamforming in reception, subsequent operations generically defined in the technical field as "back end processing" and which include, for example: the extraction of I/Q data from the reception signals subjected to beamforming, the combination of reception data relating to temporally successive transmissions, the extraction of the envelope of the received signals, the compression and decimation of the signal, the alternative processing to the generation of the B-mode image (Doppler, CFM etc), the post processing activities on the image, the scan conversion, image filtering, image enhancement and other image optimization processing, image measurements, as well as advanced imaging modalities such as elastography, attenuation imaging and others.

All or most of these processing activities can be performed by means of a hardware/software combination wherein the processing hardware is substantially traditional, for example a computer or a PC and wherein the process steps are in the form of encoded instructions in a program that is loaded and executed by said hardware.

Such a dematerialization, at least partial is already present in some diagnostic imaging devices, wherein a dedicated configuration of the electronics for processing the signals acquired by sensors/detectors/antennas is replaced by processing units with a standard electronic configuration that is capable to execute and execute one or a suite of programs wherein the instructions are encoded to make said processing unit and the related peripheral units capable of processing the acquired signals according to the provided processing steps. Therefore, the various process tasks are characterized and configured in the software code that conventional hardware performs, dematerializing the specific part of these tasks from the materialized part, i.e. from the electronics.

Centralized command and/or control systems for a plurality of imaging devices are known, for example from patent EP1262786 of the same owner. In this document a combination of several apparatuses for the acquisition of images in nuclear magnetic resonance is provided, whose control electronics are in the form of a processing unit which is provided with a communication unit with a communication network. A server is also provided connected to said communication network and has a user interface peripherals of various type, one or more memories and a program is loaded in said server wherein the instructions for managing the control units of the individual apparatuses are encoded to acquire images in nuclear magnetic resonance and to generate images from the data received from the scanners of the nuclear magnetic resonance acquisition apparatuses and optionally to execute processing processes of said images. Typically, in this configuration, where the MRI scanner, substantially the magnetic structure and the various transmitting and receiving coils, as well as the gradient coils and any further operating members is a structure that forms a patient housing compartment and that requires the patient to remain stationary on a support, such as an armchair, a bed or similar.

The connection to the communication network of the communication units associated with the MRI devices can be of the wired type, using traditional network interfaces and communication protocols, without affecting the ease of using the devices.

In the case of ultrasound probes, these are moved and manipulated on the patient by the assigned service staff and therefore the ease of use is directly related to the constraints the probe must have with the image generation unit and to the size of this same unit.

Although the arrangement of a cable of the type used in networks already define a step forward in the greater ease of handling thanks to the low number of conductors compared to those provided in the traditional cables for connecting the probes to the image generation units, a particularly advantageous solution provides the use of a communication between the ultrasound probe and the communication network of the wireless type, i.e. a wireless technology.

This type of solution is known for example from document US2015313578. In this document, a plurality of ultrasound probes each provided with a communication unit according to a wireless technology, transmits the reception signals collected during the scanning of a target under examination to a central server which is configured thanks to software in a way to be suitable for executing the typical functions of control units and image generation and/or image processing units generated by traditional ultrasound scanners.

The ultrasound screen and the input and/or command interface in this case are replaced by a plurality of display screens, preferably of the touch type, which are distributed in the environment dedicated to execute the ultrasound image acquisitions.

This solution solves in principle the problem of making it completely free from mechanical constraints and therefore of being manipulated and moved on the patient with the utmost ease and agility.

However, this system has a limitation in the fact that especially when a large number of probes operating simultaneously on different patients is provided, the system requires a considerable bandwidth and a considerable transmission speed. The two characteristics are not independent from each other, as when the bandwidth is reduced it is necessary to apply processes of multiplexing or sharing of the acquisition channels.

Attempts to integrate some circuits within the ultrasound probe are known to execute operations such as amplification, generation of the transducer command waveforms for transmission signals and/or processing of beam shaping in transmission and/or in reception with the denomination beamforming. Such integration has the purpose of reducing the quantity of signals to be transmitted by providing at one of the processing already in the probe itself.

In document US2015313578, the image is divided into frames or tiles of a smaller size than the overall image and the data transmitted by the probe to the central unit and from the central unit to the display screen are only those relating to the tiles for which there have been changes in the image represented in them.

However, such mode requires a special treatment of the images and a routine for identifying the variations in the content of the various tiles at each new image frame.

SUMMARY

Problems are overcome and advantages are realized by illustrative embodiments described herein.

A multi-user system for the acquisition, generation and processing of ultrasound images is provided, which system comprises:

a plurality of ultrasound probes configured to scan patients at predetermined examination sites and equipped with a communication unit to transmit corresponding data to one or more processing unit also equipped with a communication unit;

a plurality of display and/or user interface terminals provided in the proximity of the examination sites and equipped with a communication unit for transmitting to and receiving data from one or more of said processing units and/or from one or more of said probes;

a communication network which connects the communication units of the probes, of the display and user interface terminals and of said one or more processing units;

said probes and said display and/or user interface terminals being each identified by a corresponding ID and;

said one or more processing units being designed to perform each at least part of the processing steps of the transmission and reception signals for the acquisition, generation and processing of images from said reception data, said processing units being defined by a processing hardware comprising at least one processor, at least one memory, at least one communication unit in transmission and reception, at least one input port and one output port for data and/or commands, at least one program being loaded into said processing units wherein the instructions to execute are encoded, making said processing unit or units capable of carrying out the at least one or more processing steps for transmission and reception signals for the acquisition, generation and processing of images from said reception data.

BRIEF DESCRIPTION OF THE DRAWINGS

These and other features and advantages of example embodiments of the present disclosure will become more clearly apparent from the following description of some embodiments illustrated in the accompanying drawings wherein.

4

Figure 3:
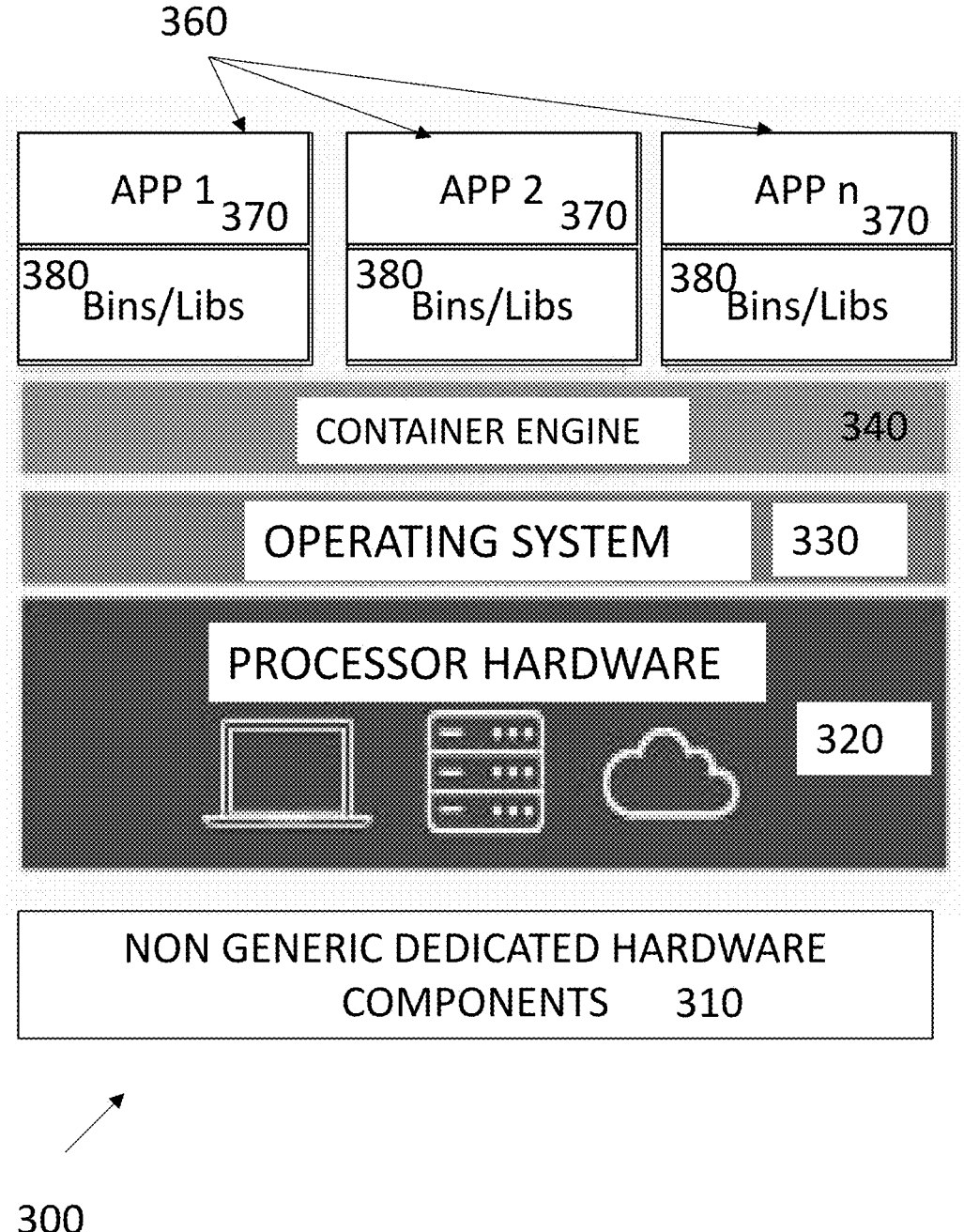

The FIG. 3 shows a high-level block diagram of an architecture of a hardware software system according to the technology called containerization.

Figure 2:
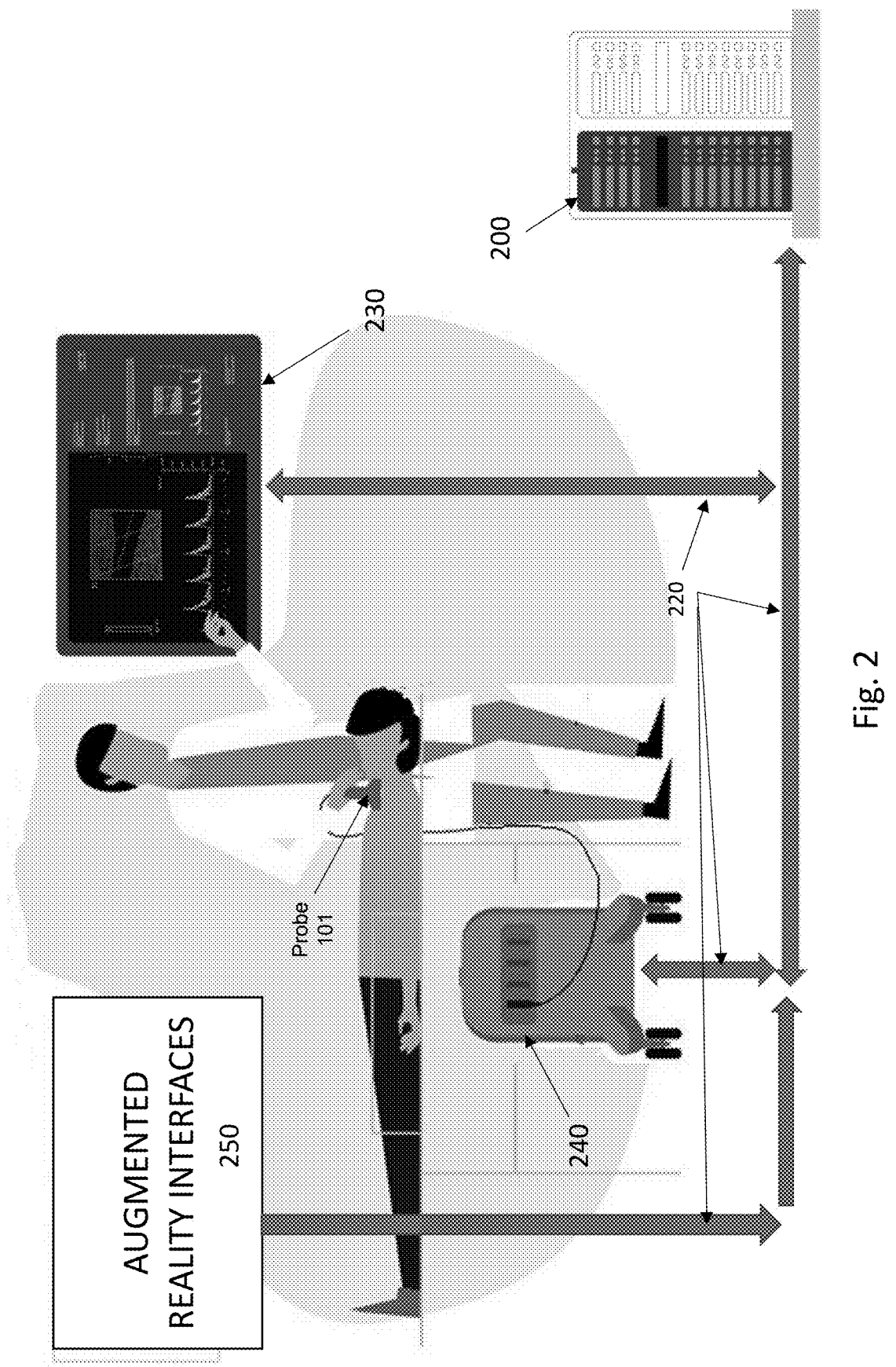
FIG. 2 shows an embodiment of a possible hardware configuration of the ultrasound system according to the present disclosure.

FIG. 4A shows with a graphic in the form of some tables different possible configurations of an ultrasound system according to the present disclosure and in particular according to FIG. 2 and the corresponding variants wherein possible different subdivisions of the front-end processes, image forming, back-end and further processing of an ultrasound imaging system are shown, being the items of the processes to be interpreted as specific software loaded and by execution processing unit provided in the probe, in the processing location, in the central processing unit and in the display terminal and of user interface.

FIG. 4B shows a variant relating to the configuration wherein a local processing unit is not provided and the probe 101 communicates directly with the central unit 200.

Figure 5:
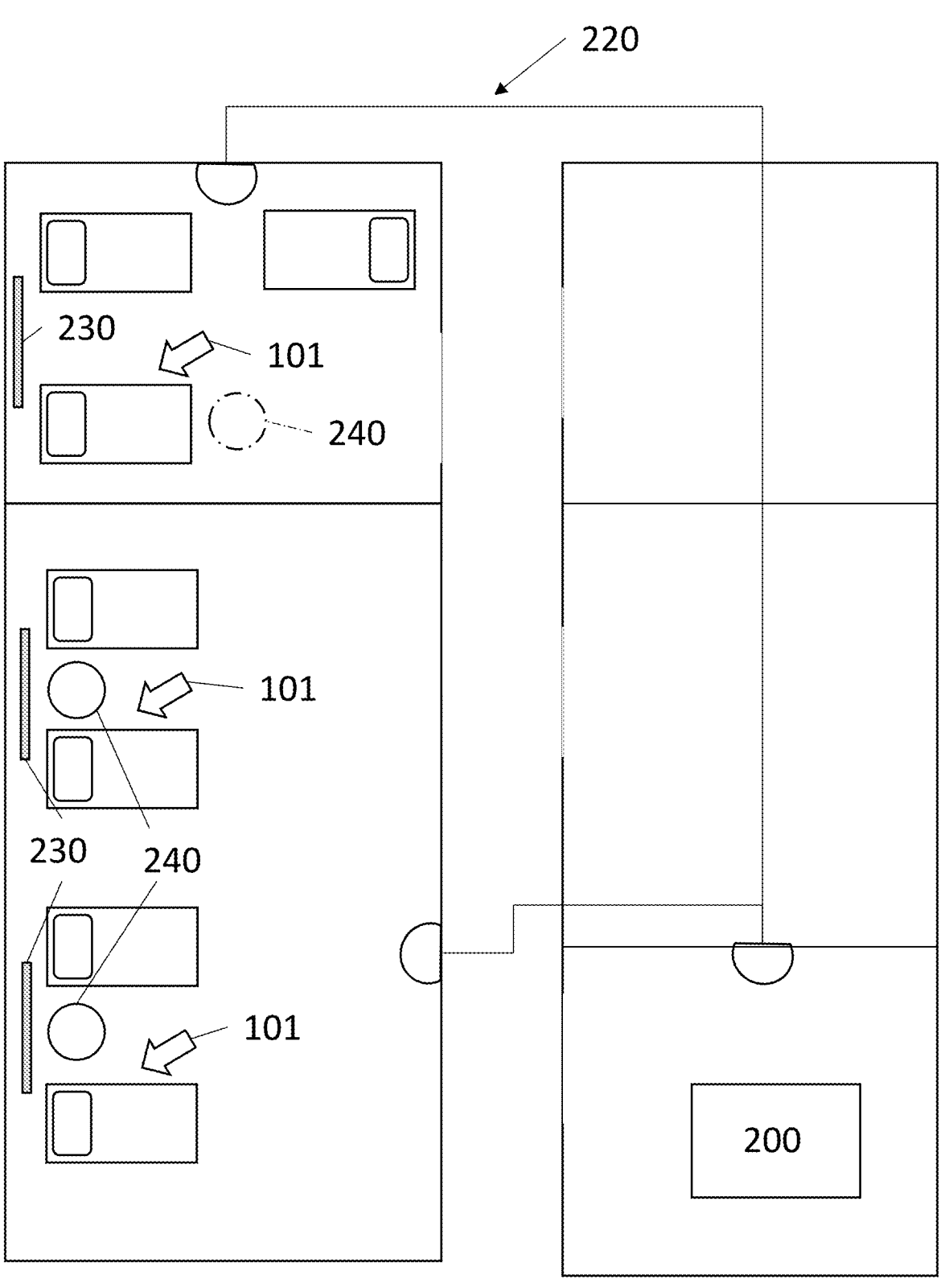

FIG. 5 schematically shows an example of system installation in a hospital.

DETAILED DESCRIPTION OF ILLUSTRATIVE EMBODIMENTS

A further limitation of the solution to the state of the art consists in the fact that in any case, even if at an experimental and prototype level there is the possibility of realizing a device actually working, such a device is very far from being used concretely in current medical practice and the development of a device mature for use requires still a long time for a series of technical reasons that go beyond the mere limitation of bandwidth.

Typically, a generic probe for the acquisition of ultrasound images comprises a set of electroacoustic transducers, each of them emits ultrasonic waves when it is supplied with an electrical excitation signal and further generates an electrical reception signal when on the same it comes to affect a pulse or ultrasonic wave that can be generated by the reflection of the ultrasonic waves emitted by the same transducer. The set of transducers is provided with at least one communication line with a processing unit through which each transducer supplies the reception signals to the transmission unit itself, and with a communication line through which are transmitted to each transducer the electrical excitation signals produced by a generating unit for the excitation of each single transducer upon the emission of ultrasonic waves, which generating unit comprises means for generating the excitation signals and means for supplying said signals to said set of transducers.

An ultrasound imaging system can be divided into a front-end (FE), an image former (IF) and the back-end (BE). The FE manages the hardware aspects of the transducer, the generation of transmission pulses (TX), the reception of the analogue signal (RX) and a commutation matrix (SM) for the transmission (TX) and reception (RX) phases. The image former is responsible for beamforming, and sometimes this function is subdivided between the IF image former and the FE front end. The function of the Back-End is to enhance the images, convert them from acoustic scan grids to display grids, then render and display said images.

Recently, IF and BE have often combined in software using raw data directly.

This method requires several high-speed communication channels communication method, in general, based on high-speed technology to transfer raw data to a workstation equipped with high performance CPU and GPU.

The amount of data to be transferred from the Front-end FE to the BE Back-end BE is considerable and for example for a high-end system with 128 channels, operating at 40 MHz sampling frequency, encoded at 12-bit per sample, each transmit TX pulse event generates a raw data size of 2,212 MB for an axial image of 7.7 cm at a sound speed of 1540 m/s. Considering a repetition of pulses of for example 15,400 times per second as in ultrafast imaging, the data to be transferred are of the order of magnitude of 18.8 GB/s. Such orders of magnitude make difficult or at least only theoretical the implementation of a system for ultrasound imaging, for example, such as the one described in the document US2015313578.

Figure 1:
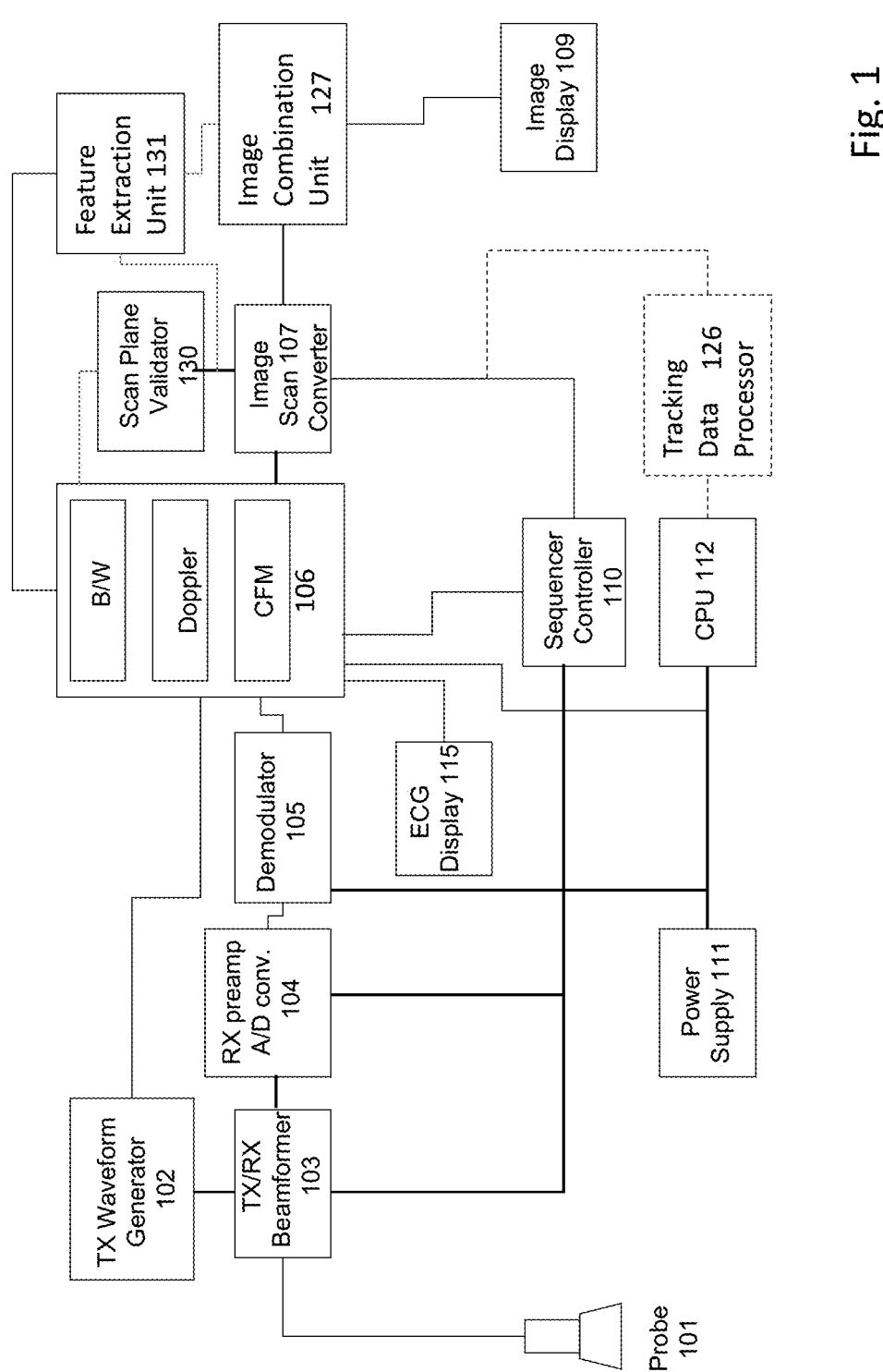
FIG. 1 shows a high-level block diagram of an ultrasound image acquisition system according to the state of the art.

FIG. 1 shows a high-level block diagram of a system for acquiring ultrasound images according to the state of the art. This system is shown without any limiting purpose, but only for illustrative purposes to define a consolidated state of the art, wherein the ultrasound system shown is combined in a single device stand alone.

Probe 101 can include various transducer array configurations, such as one-dimensional array, two-dimensional array, two-dimensional array, linear array, convex array and the like. Array transducers can be managed as 1D array, 1.25D array, 1.5D array, 1.75D array, 2D array, 3D array, 4D array, etc.

The ultrasound probe 101 is coupled via a wired or wireless connection to a beamformer 103. The term beamformer refers to a device for forming a beam of ultrasonic pulses, which pulses are each one generated by one of the transducers of the set of transducer which forms the probe. Since with respect to a point arranged inside an area to be examined the distance of each of the transducers of the probe is different and considering the speed of the acoustic wave substantially constant in the region under examination crossed by the ultrasonic pulses to reach said point, the times necessary for the various pulses generated respectively by one of the transducers of the probe, are different and to focus said pulses on the point under examination so that said pulses are constructively combined it is necessary that they reach the predefined point at the same instant and possibly with the same phase. Such process is not only typically executed in the transmission phase, but also in the reception phase. In fact, also in this case, the acoustic pulses reflected from a point inside the body under examination and for which a substantially homogeneous transit speed in said body under examination is supposed, reach the various transducers at different times due to the different length of the path between each transducer and the reflection point. In order to reconstruct the overall contribution of the reflected wave, it is therefore defined to temporally realign the contributions of the individual pulses received by the individual transducers to obtain their constructive combination.

There are various focusing techniques in transmission and reception that allow to reduce the computational effort of this process, both as regards the necessary hardware and as regards the processing times for the formation of the transmission and/or reception beam.

The beamformer 103 according to the state of the art therefore comprises a transmission beamformer (TX) and/or a receiving beamformer (RX) which are jointly represented by the beamformer TX/RX 103. The TX and RX parts of the beamformer can be implemented together or separately. The beamformer 103 supplies transmission signals to the probe 101 and execute the beamforming of the "echo" reception signals received by the probe 101 according to the expected reception and/or transmission beam formation mode.

A TX waveform generator 102 is coupled to the beamformer 103 and generates the transmission signals which are provided by the beamformer 103 to the probe 101. The transmission signals can represent various types of ultrasonic TX signals, such as those used in connection with B-mode imaging, Doppler imaging, color Doppler imaging, pulse inversion transmission techniques, contrast-based imaging, M-mode imaging, and the like. Additionally or alternatively, transmission signals can include single or multi-line transmission, transmission pulses can be focused on single lines or can be focused to extend over wider areas or an entire region of interest (called in technical jargon ROI), for example in the form of plane waves or the transmission pulses can be unfocused and made up of pulses transmitted by a single point, i.e. by a single transducer of the set of transducers at a time or by a selected subgroup of transducers or even by all the transducers of the set of transducers of the probe which are controlled in transmission so as to generate a pulse or a wave or a sequence of transmission pulses configured as if they were emitted from a common physical point of view or from multiple single points, i.e. transducers or from more subgroups of transducers.

The beamformer 103 executes beamforming on echo signals received to form reception echo signals deriving from the received signal contributions received by the individual transducers, in connection with the positions of the pixels distributed in the region of interest. For example, in accordance with certain embodiments, the transducer elements generate raw analogue reception signals which are provided to the beamformer. The beamformer adjusts the delays to focus the reception signal along one or more selected reception beams and at one or more selected depths within the region of interest (ROI). The beamformer adjusts the weighting of the received signals to achieve the desired apodization and profile. The beamformer applies weights and delays to the reception signals of the individual corresponding transducers of the probe. The delayed and weighted reception signals are then added together to form a coherent reception signal.

The beamformer 103 includes (or is coupled to) a pre-amplifier and/or A/D converter 104 which digitalizes the reception signals at a selected sampling frequency rate. The digitalizing process can be executed before or after the summing operation which produces the coherent reception signals. The beamformer also includes (or is coupled to a demodulator 105 which demodulates the reception signals to remove the carrier waveform. Once the reception signals are demodulated and digitalized, complex reception signals are generated which include components I, Q (also called I, Q data pairs). The I, Q data pairs are stored in memory as image pixels. I, Q data pairs, which define the image pixels for the corresponding individual positions along the corresponding lines of sight (LOS) or lines of sight A collection of image pixels (e.g. data pairs I, Q) are collected over time and saved as 2D frames and/or 3D volumes of image data. The pixels of the image correspond to the tissues and other anatomies within the ROI.

Optionally, it is possible to program a dedicated sequence/timing controller 110 to manage the timing of the acquisition, which can be generalized as a sequence of shots aimed at selecting reflection points/targets in the ROI. The sequence controller 110 manages the operation of the TX/RX beamformer 103 in connection with the transmission of ultrasonic beams and the measurement of the image pixels in the individual LOS positions along the lines of sight. The sequence controller 110 also manages the collection of the reception signals.

One or more processors 106 and/or CPU 112 execute various processing operations as described herein.

For example, processor 106 executes a B/W module to generate B-mode images. Processor 106 and/or CPU 112 executes a Doppler module to generate Doppler images. The processor executes a Colour flow module (CFM) to generate coloured images. Processor 106 and/or CPU 112 may implement additional ultrasound imaging and measurement operations. Optionally, the processor 106 and/or the CPU 112 can filter the first and second displacements to eliminate motion related artifacts.

An image scan converter 107 executes image pixel scan conversion to convert the pixel format of the image from the ultrasound acquisition signal path coordinate system (e.g., the beamformer, etc.) and from the display coordinate system. For example, the scan converter 107 can convert image pixels from polar coordinates to Cartesian coordinates for frames.

A cine memory not shown in detail stores a timeline of frames. Frames can be stored in polar coordinate formats, Cartesian coordinates or in another coordinate system.

An image display 109 displays various ultrasound information, such as frames and information measured according to the embodiments contained herein. The display 109 shows the ultrasound image with the region of interest indicated.

A control CPU module 112 is configured to execute various tasks such as user/interface implementation and general system configuration/control. In the case of a fully software implementation of the ultrasonic signal path, the processing node usually also houses the functions of the control CPU.

A power supply circuit 111 is provided for powering the various circuits, modules, processors, memory components and the like. The power supply 111 may be an alternating current power source and/or a battery power source (e.g., in connection with portable operation).

According to the present embodiment and by way of example, the processor 106 can be associated or possibly also comprise an ECG monitoring module which receives the signals of an ECG (not shown in detail) and which allows to combine the acquisition of images with the ECG signals according to the different variants of known techniques for acquiring images synchronized by means of an ECG signal.

The purpose of example embodiments of the present disclosure is to provide a system of the type described at the beginning, wherein it is possible to overcome not only the problems associated with the bandwidth of the wifi channels or other wireless communication system and the transmission speed of the signals between the probe and the processing unit and/or said processing unit and the display terminals, as well as between the user interfaces and said processing unit, but also to overcome drawbacks related to the effective possibility of concretely realizing a mature device for the market and its use by expanding and improving its functionality.

According to a first aspect of an example embodiment of the present disclosure, the above problem is solved by providing Multi-user system for the acquisition, generation and processing of diagnostic images which system includes:
- a plurality of ultrasound probes configured to scan patients in predetermined examination sites and equipped with a communication unit to transmit the corresponding data to one or more processing units also equipped with a communication unit;
- a plurality of display and/or user interface terminals provided in the vicinity of the examination sites and provided with a communication unit for transmitting to and receiving data from one or more of said processing units and/or from one or more of said probes;
- a communication network which connects the communication units of the probes, of the display and user interface terminals and of said one or more processing units;
- said probes and said display and/or user interface terminals each being identified by a corresponding ID and;
- said one or more processing units being designed to execute each at least part of the processing steps of the transmission and reception signals for the acquisition, generation and processing of images from said reception data,
- said processing units being provided with a processing hardware comprising at least one processor, at least one memory, at least one communication unit in transmission and reception, at least one input port and one output port for data and/or commands,
- in said processing units being loaded at least one program wherein the instructions to execute are encoded, making said processing unit or units capable of executing the at least one or more processing steps for transmission and reception signals for the acquisition, generation and processing of images from said reception data;
- and wherein each processing step and/or a group of two or more processing steps are in the form of containers comprising the application that contains the instructions for the execution of the processing step or steps to the processing unit and the environment execution of the application with the relative settings, the libraries and the API interface connections necessary for the execution of the application,
- a management program being loaded and being executed into processing units which defines the container engine.

In one embodiment, the system has a distributed hardware architecture of the processing unit, comprising at least two, preferably three, optionally at least four or more processing units which are each integrated, respectively, in the probe and/or in an optional unit processing room associated with one or more patient stations and dedicated to a single probe or to a partial number of probes and possibly positioned in the immediate vicinity of said one or more patient stations and/or in a remote central processing unit which is associated with all and/or at least part of said probes and/or said local processing units, and/or one or more of said plurality of display and user interface terminals,
- said processing units being communicating with each other;
- and the processing steps of the reception signals of the probe or probes being divided on said processing units in such a way that one or more of said processing units executes only a part of the processing steps.

According to an embodiment, applications are provided, each of which applications is included and executable in a corresponding container or at least two of which applications are included and executable in a corresponding container and each of which applications comprises the code for executing respectively at least one of the processing steps that can be selected or provided for in the following list:
- calculation of the transmission timing;
- generation of digital transmission signals;
    - D/A (digital/analogue) conversion of transmission signals;
    - A/D (analogue/digital) conversion of the received signals;

beamforming in reception;

subsequent operations generically defined in the technical field as "back end processing" as one or more of the following steps, for example:

extraction of I/Q data from the reception signals subjected to beamforming;

combination of reception data relating to temporally successive transmissions;

extraction of the envelope of the reception signals;

compression and decimation of the signal; alternative processing to image generation B-mode, Doppler, CFM and other modes;

post processing activities on the image;

scan conversion;

image filtering; image enhancement and other image optimization processing, measurements on image, as well as advanced imaging modalities such as elastography, attenuation imaging and combinations of one or more of the aforementioned steps listed.

According to an embodiment, the probe(s) and/or the local processing unit(s) and/or the central processing unit(s) and/or the display and/or user interface terminal(s) can communicate alternatively or in combination, thanks to a selection of the communication mode, via a cable connection and/or a wireless connection.

According to another feature, it is possible to provide a local unit associated with a group of patient stations, for example two or more patient stations, a probe being provided for each station and/or for two or more stations of said group.

Similarly, it is possible to provide a central processing unit which operates in combination with one or more groups of patient stations, i.e. probes and/or local processing units.

Different system configurations are possible according to the more general combination mentioned above.

According to one embodiment, a configuration of the system provides that at least one of the probes is connected to a local processing unit via analogue cable;

D/A conversion in transmission (TX), A/D conversion in reception (RX) is executed on a local processing unit and beamforming in transmission and/or reception (TX/RX) and further processing according to one or more of the steps listed above on a central processing unit.

An executive variant alternatively provides that at least one of the probes is connected to a local processing unit via analogue cable;

D/A conversion in transmission (TX), A/D conversion in reception (RX) and beamforming in transmission and/or reception (TX/RX) on a local unit and further processing on a central processing unit.

According to a further embodiment, a configuration of the system provides that at least one probe is wired a wired or wirelessly connected to a local processing unit with a digital connection;

D/A conversion in transmission (TX), A/D conversion in reception (RX) is executed on the probe and the beamforming in transmission and/or reception (TX/RX) and the back-end processing on a unit of local processing and further processing according to one or more of the steps listed above on a central processing unit.

An executive variant alternatively provides that at least one probe is wired or wirelessly connected to a local processing unit with a digital connection;

D/A conversion in transmission (TX), A/D conversion in reception (RX) and beamforming in transmission and/or reception (TX/RX) are executed on the probe and the back-end processing on a unit of local processing and further processing according to one or more of the steps listed above on a central processing unit.

Yet another executive variant alternatively provides that at least one probe is wired or wirelessly connected to a local processing unit with a digital connection;

D/A conversion in transmission (TX), A/D conversion in reception (RX) are executed on the probe, while the beamforming in transmission and/or reception (TX/RX) are executed partly on the probe and partly on a local processing unit and the back-end processing on a local processing unit and the further processing according to one or more of the steps listed above on a central processing unit.

A further embodiment provides that at least one probe is connected to a local processing unit by cable and with an analogue or digital connection;

transmission signal generation and transmission beamforming are executed on the probe, A/D conversion in reception (RX) and beamforming in reception are executed on a local unit, back-end processing and further image processing are executed on a local or central unit.

An executive variant alternatively provides that at least one probe is connected to a local processing unit by cable and with an analogue or digital connection;

generation of transmission signals, beamforming in transmission and beamforming in reception, partial analogue are executed on the probe, A/D conversion in reception (RX) is executed on a local unit, while further beamforming steps, the back-end processing and further image processing are executed on a local or central unit and some further processing steps are performed only on a central unit, executing on said units the corresponding application included in a container dedicated to it.

An executive variant may provide that the local processing unit or units are omitted and that the functions executed by that or them according to any of the forms and executive variants described above are executed by the probe and/or by a central processing unit or that said functions are divided between the probe and said one central processing unit.

According to an embodiment, for example, the probe can comprise a DAC and/or ADC conversion unit.

Alternatively, different variants are possible according to which the probe can comprise a DAC/ADC conversion unit and a transmission and/or reception beamforming unit, or alternatively a DAC/ADC conversion unit, a transmission and/or reception beamforming unit and back-end processing unit, or according to yet another alternative, a beamforming unit in transmission and/or reception, one or more back-end processing units and a scan converter, as well as optionally an execution unit of further processing of the images, in this case only the ultrasound images already formed being transmitted to a central processing unit.

Although this configuration of the system which provides for a plurality of processing units on which at least part of the various processing tasks of the reception and/or transmission signals are distributed, can help in reducing the data to be transmitted between the probes, the local and central processing units and the display terminals and/or user interface and therefore in a limitation of bandwidth occupation, especially for solutions that provide for a connection using wireless protocols, it is important to be able to combine with one or more any of the embodiments and of the executive variants of the above measures that may further limit the amount of data transmitted between the probe or probes, the local processing unit or units, the central processing unit or units and the display and/or user interface terminal or terminals.

According to an embodiment that can be provided in any combination or sub-combination with one or more of the embodiments and executive variants described above of the present disclosure, the system further provides to apply alternatively between them and/or, when possible, also in any combination of one or more processes to reduce the amount of data selected from the following list:

Adaptive time decimation of the data, according to a predetermined bandwidth, by adjusting the sampling frequency according to the Nyquist limit (twice the maximum frequency for RF data, maximum frequency-minimum frequency for IQ data);

Use of a subset of receiving transducers, calculated based on the maximum aperture in reception actually used to combine the signals relating to a given transmission;

Under sampling, periodic or aperiodic, in the time domain or in the domain of the receiving channels or in both and use of compress sensing techniques for image reconstruction based on sparse priorities in the image domain or in a transformed domain such as for example fourier transform, k-space, wavelet;

Under sampling, periodic or aperiodic, in the time domain or in the domain of the receiving channels or both, and use of machine learning techniques for the reconstruction of missing data;

Under sampling by reducing the number of data by multiplying the signals received by a matrix with a number of rows lower than the number of columns;

use of advanced beamforming techniques that allow to obtain images of equal or similar quality compared to standard line by line isolation, reducing the number of transmissions and therefore the amount of data necessary to form a frame, such as those in the following list: multiline beamforming in reception, synthetic transmit beamforming (STB), retrospective transmit beamforming (RTB), synthetic aperture imaging, plane wave or diverging wave beamforming;

combination of beamforming based on synthetic aperture or plane wave or diverging wave beamforming, with a reduction in the number of transmissions and with a machine learning algorithm that maps the low-quality images obtained with a limited number of insonifications, on images that reproduce the high quality image characteristics that would have been obtained with a higher number of insonifications.

two-stage beamforming or micro-beamforming wherein part of the beamforming is executed on the probe on distinct groups of transducers, thus reducing the number of communication channels between the probe and the apparatus and consequently the data transfer rate, and wherein the further part of the beamforming is executed by a local and/or central processing unit, the instructions for the execution of said processes being codified in one or more corresponding applications included and executable each or a plurality of these in a corresponding container.

An RTB beamforming method is described in EP3263036.

A description of Synthetic Aperture Beamforming is contained in the publication J. A. Jensen, S. I. Nikolov, K.

L. Gammelmark, and M. H. Pedersen, "Synthetic Aperture Ultrasound Imaging," Ultrasonics, vol. 44, pp. e5-e15, 2006.

Document US2014058266A1 also describes a specific application based on Synthetic Aperture Imaging.

A further description of the beamforming protocol called Synthetic Aperture Imaging is contained in the document "Synthetic Aperture and Plane Wave Ultrasound Imaging with Vesrsal ACAP". Published and available at the web address https://www.xilinx.com/ . . . /white_papers/wp520-sa-pw-imaging.pdf.

The Plane Wave Beamforming technology is described in the document "Synthetic Aperture and Plane Wave Ultrasound Imaging with Vesrsal ACAP" published and available at the web address https://www.xilinx.com/ . . . /white_papers/wp520-sa-pw-imaging.pdf.

The beamforming technique by means of "back propagation" is described for example in documents U.S. Pat. Nos. 5,628,320 and 5,720,708 which comprise a detailed and exhaustive description of the theory and method of back propagation and whose information content is understood to be integrated by reference in this description.

An example of a process using a Convolutional Compounding algorithm is described in the document Sparse convolutional plane-wave compounding for ultrasound imaging, Baptiste Heriard-Dubreuil, Adrien Besson Frédéric Wintzenrieth, Jean-Philippe Thiran and Claude Cohen-Bacrie, [Proceedings of IUS 2020], Conference2020 IEEE International Ultrasonics Symposium (IUS 2020), Las Vegas, US, Sep. 6-11, 2020.

The technique called Compressed Sensing is based on the structure of signals in order to reduce the number of samples needed to reconstruct a signal, compared to Nyquist's law. The fundamental principle of CS is to measure only a few fundamental coefficients of a compressible signal and then to reconstruct it by means of an iterative optimization process.

An imaging method and system that uses beamforming technology by means of a Compressed Sensing technique are described in document EP2660618A1 which is integrated by reference in the present description and forms an integral part of it.

An example of microbeamforming is described in US20080262351A1 which is incorporated in the present description by reference.

According to yet another embodiment that can be provided in combination with one or more of the previous embodiments and variants, it is possible to apply machine learning techniques for the beamforming phase in reception.

These machine learning or deep learning techniques can be used to reconstruct image data with a certain quality even in the presence of a small number of transmissions.

Examples of these techniques are described in the documents "A Deep Learning Approach to Ultrasound Image Recovery", Dimitris Perdios, Adrien Besson, Marcel Arditi, and Jean-Philippe Thirany, 2017 IEEE International Ultrasonics Symposium (IUS) or "CNN-Based Image Reconstruction Method for Ultrafast Ultrasound Imaging", Dimitris Perdios, Manuel Vonlanthen, Florian Martinez, Marcel Arditi, and Jean-Philippe Thiran, IEEE Transactions on Medical Imaging (Volume: 40, Issue: 3, March 2021), Page(s): 1078-1089.

The use of image reconstructions using artificial intelligence algorithms has been known for decades in the field of imaging.

An embodiment that can be provided in any combination or under combination with the techniques for reducing the amount of data described above and which involves the use of Machine Learning algorithms can provide for the use of such algorithms to reduce and better define the size of a ROI with reference to a target of interest present in the body under examination and/or alternatively or in combination with the definition and choice of scanning planes.

Even in the case of applications that contain instructions to perform one or more of the processes listed above, these applications are included in a container and run within the environment defined by said container.

As regards the management of the communication between two or more probes and/or two or more local processing units and/or at least one central processing unit and/or one or more display and user interface terminals, an embodiment of the present disclosure provides that said communication is based on protocols as well as on a virtual 5G network and/or communication via optical fiber.

A description of a 5G telecommunications virtual network that can be applied to this ultrasound system is described in the document https://cordis.europa.eu/article/id/238330-novel-5g-architecture-based-on-virtual-networks/it.

According to an embodiment which can be provided in combination with one or more of the previous embodiments described above, at least some of the display and/or user interface terminals comprise or include an interface device for augmented reality.

For example, and not limited to, the augmented reality device can comprise one or more of the units listed in the following non-exhaustive list:

Surface Studio and Dial®, Azure Kinetic DK, Intel Real Sense, Speech recognition, HoloLens, gesture recognition, gaze orientation recognition or a combination of these.

According to a further embodiment which can be provided in any combination or sub combination with one or more of the previous embodiments and variants, the system has at least one memory for the patient data corresponding to the images and at least one processing step which provides for allowing the access to patient data after authentication and authorization, while provide access and transmission in anonymized form, i.e. without personal information of the patient or patients, to other post processing units, such as a remote work station for a 2nd opinion diagnosis, i.e. an additional diagnosis with respect to a local diagnosis.

With reference to the architecture of the system that provides for a containerization, wherein the individual containers each contain one or more of the application software wherein the instructions for the execution of at least one or a certain number of processing steps are encoded for the acquisition and generation and also for image processing, it appears evident how such an architecture allows users to freely configure different classes of ultrasound systems and therefore to calibrate the systems and the related costs with reference to the desired use. For example, container-based applications can be related to systems that have different numbers of BF channels, a different band, a different sampling rate and/or a different Max gain. Each different application having a corresponding cost and therefore allowing to calibrate the system and the performances and also the cost to the actual needs.

In particular, having the basic hardware available, a user can purchase licenses for different applications and these licenses can also be time-based or for use, making high-level configurations accessible only for cases wherein are necessary and for the time wherein such services are required.

These and other characteristics and advantages of example embodiments of the present disclosure become clearer from the description of some executive examples illustrated in the attached drawings wherein:

FIG. 1 shows a high-level block diagram of an ultrasound image acquisition system according to the state of the art.

FIG. 2 shows an embodiment of a possible hardware configuration of the ultrasound system according to the present disclosure.

The FIG. 3 shows a high-level block diagram of an architecture of a hardware software system according to the technology called containerization.

FIG. 4A shows with a graphic in the form of some tables different possible configurations of an ultrasound system according to an example embodiment of the present disclosure and in particular according to FIG. 2 and the corresponding variants wherein the possible different subdivisions of the front-end processes, image forming, back-end and further processing of an ultrasound imaging system are shown, being the items of the processes to be interpreted as specific software loaded and by execution processing unit provided in the probe, in the processing location, in the central processing unit and in the display terminal and of user interface.

FIG. 4B shows a variant relating to the configuration wherein a local processing unit is not provided and the probe 101 communicates directly with the central unit 200.

FIG. 5 schematically shows an example of system installation in a hospital.

With reference to FIG. 2, the ultrasound system according to an example embodiment of the present disclosure comprises a probe for transmitting the ultrasound pulses in a body under examination and for receiving the echo signals generated by said transmission pulses. The probe is part of the so-called Front-End of the system. The probe indicated with 101 is connected via cable or wireless connection with a local processing unit indicated with 240.

The local processing unit 240 in turn is connected via a wireless connection with a communication network 220 to a central processing unit 200. A display terminal and input interface for the user, for example a touchscreen 230 it is also connected via wireless connection to the wireless network 220 to receive the images to be displayed from the central unit 200 and/or to transmit a probe the commands from the user to or more of the central units 200, local unit 240 and/or 101.

An embodiment variant may provide that the probe 101 is also connected to the network 220 by means of a wireless connection instead of by means of a cable. In this case, the probe can connect either to the local processing unit 240 and as in FIG. 2, or at the same time also directly to the processing unit 200 and/or to the display terminal and user interface 230.

For example, for setting or diagnostic operations, the probe connects directly to the display terminal 230 when it operates with a wireless connection, while it must be connected through the local unit or the central unit if it operates with a configuration like the one illustrated.

The hardware structure of the operating units, such as the probe 101, and/or the local processing unit and/or the central processing unit and/or the display and user interface terminal, have a part of the hardware comprising a conventional processor, as for example a microprocessor with its standard peripherals and/or a CPU with its standard peripherals or a computer such as a PC or a workstation. Only a part of the hardware must necessarily comprise ad hoc components such as transducers, screens and more.

A solution of this type of architecture is suggested by document EP1262786, whose description is included by reference in the present description.

Thanks to the possibility of structuring the hardware of these operating units as a generic universal and programmable processing system, it is possible to realize the specific functions of acquisition, processing of the transmission and reception signals and the relative functions of image formation, as well as the their processing function means for further obtaining measures, additional information on chemical and/or physical and/or qualitative parameters of the target under examination by means of software wherein the task workflows are encoded, i.e. the sequence of instructions to be executed by the processing hardware that allow this hardware and its peripherals to execute the aforementioned functions.

Therefore, the migration of the ultrasound hardware architecture from an ad hoc system to a system comprising standard processing hardware that executes specific programs wherein the specific data processing functions are coded for the various steps of the acquisition, training and image processing processes that allow to release the functions of the ultrasound from the hardware structure, making it very flexible to allow the configuration of the ultrasound itself.

Typically, the main functions executed by an ultrasound system comprise various processing steps which include, in a non-exhaustive and not even limiting way, the calculation of the transmission timing, the generation of digital transmission signals, the D/A conversion (digital/analogue) of the transmission signals, A/D (analogue/digital) conversion of received signals, beamforming in reception and/or transmission, subsequent operations such as data extraction by I/Q demodulation, the combination of reception data relating to transmissions temporally successive, the extraction of the envelope of the reception signals, the compression and/or decimation of the signals (step conventionally summarized as "back end processing"), the alternative processing to the generation of the B-mode image, such as Doppler, CFM and others known at the state of the art, post processing on the image, scan conversion, image filtering, image enhancement and others, measurements on the the image, advanced imaging modalities such as elastography, attenuation imaging and others.

It should be noted that thanks to the migration of functionalities in the form of software, a system according to the present disclosure can easily be adapted or modified or integrated to execute the aforementioned processes in ways that will be developed in the future, as well as to be able to execute new processing functions that will be developed in the future.

Thanks to the fact that a conventional processing unit can be provided in each of the operating units previously described with reference to FIG. 2, an example embodiment of the present disclosure allows the steps of generating the transmission signals, acquisition and processing of the reception signals listed above to be divided between the aforementioned operating units.

The type of steps to be executed by each of the aforementioned operating units depends in particular on the type of connection of said operating units to each other. As appears from FIG. 2, in fact, the connection, preferably of the probe to a local processing unit, can take place either by means of a wired connection or by means of a wireless connection. This results in limitations on the data transmission speed and especially on the bandwidth available for the transmission of this data.

As regards the available bandwidth and therefore a specific distribution of processes on the different components of the system, i.e. probe, local processing unit, central processing unit and display and user interface terminal, it is clear that the choice of this distribution depends above all on the number of probes, local processing units and display and interface terminals that must be connected simultaneously to a common central processing unit, directly or through its own dedicated local processing unit or possibly through a local processing unit shared by at least part of said probes.

It is worth highlighting here the fact that it is possible to configure the system in such a way that the processing sections associated with each operating unit or component of the system (probe, local processing unit, central processing unit, display terminal and interface) can be configured in such a way as to execute multiple processing steps, the corresponding software being loaded into their memories, while it is possible to dynamically modify the processing steps performed by the various operating units, between a minimum and a maximum of said steps, depending on the bandwidth available for communication between them.

This dynamic configuration mode as a function of bandwidth can be controlled by software that checks the available transmission speed and disables some processes in one of the operating units, enabling it at the same time in another.

The dynamic transfer of processing steps from one to the other of the operating units of the ultrasound system can also take place in function, for example of the residual power supply for one or more of said operating units when the power supply of this or of these are not from the network, but from the battery or accumulator.

Similarly to the software for executing the processing steps of the transmission and/or reception signals for the acquisition, formation and processing of the images, in one or more or in all aforementioned operative units, programs for executing specific operations to reduce the amount of data can be stored.

A non-exhaustive list of the main possible processes for limiting the amount of data is, for example:

Adaptive time decimation of the data, according to a predetermined bandwidth, by adjusting the sampling frequency according to the Nyquist limit (twice the maximum frequency for RF data, maximum frequency-minimum frequency for IQ data);

Use of a subset of transducers in reception, calculated based on the maximum receiving aperture actually used to combine the signals relating to a given transmission;

Under sampling, periodic or aperiodic, in the time domain or in the domain of the receiving channels or in both and use of compress sensing techniques for image reconstruction based on sparse priorities in the image domain or in a transformed domain such as for example fourier transform, k-space, wavelet;

Under sampling, periodic or aperiodic, in the time domain or in the domain of the channels in reception or both, and use of machine learning techniques for the reconstruction of missing data;

Under sampling by reducing the number of data by multiplying the signals received by a matrix with a number of rows lower than the number of columns;

use of advanced beamforming techniques that allow to obtain images of equal or similar quality compared to standard line by line insonifications, reducing the number of transmissions and therefore the amount of data necessary to form a frame, such as those in the following list: multiline beamforming in reception, synthetic transmit beamforming (STB), retrospective transmit beamforming (RTB), synthetic aperture imaging, plane wave or diverging wave beamforming;

combination of beamforming based on synthetic aperture or plane wave or diverging wave beamforming, with a reduction in the number of transmissions and with a machine learning algorithm that maps the low-quality images obtained with a limited number of insonifications, on images that reproduce the high-quality image characteristics that would have been obtained with a higher number of insonifications;

two-stage beamforming or micro-beamforming wherein part of the beamforming is executed on the probe on distinct groups of transducers, thus reducing the number of communication channels between the probe and the apparatus and consequently the data transfer rate, and wherein the further part of the beamforming is executed by a local and/or central processing unit, the instructions for the execution of said processes being encoded in a corresponding program which is loaded and executed by the processing unit of the probe(s) and/or of the local unit(s) and/or of the central unit(s) and wherein the execution of said program configures said processing units and the associated peripherals to execute the functions of the aforementioned one or more processes for reducing the amount of data to be transmitted between said probe(s) and/or the said local processing unit(s) and/or said central processing unit or units.

These data quantity reduction processes have been described in greater detail in the previous description with reference also to published documents which are to be considered included in the present description.

In FIG. 2, the reference number 250 generically indicates a box which refers to augmented reality systems which can be provided in combination and/or as an alternative to the display and user interface terminal 230.

In the figure, this term also indicates any type of interface that allows the user to operate without using traditional interface systems such as a keyboard or mouse, such as voice recognition or gesture recognition systems.

Possible augmented reality systems are listed in the following list which is only illustrative and not exhaustive:

Surface Studio and Dial®, Azure Kinetic DK, Intel Real Sense, Speech recognition, HoloLens, gesture recognition, gaze orientation recognition or a combination of these.

Also for these systems it is possible to provide a wired or wireless connection with the remaining units of the ultrasound system depending on the contingent conditions.

The element of augmented reality can comprise the so-called Holo Lens with which the doctor can perform the examination by looking at the patient and viewing the ultrasound image, thus allowing for maximum ergonomic efficiency. Using gesture and/or eye movement detection systems, it is also possible to provide a user interface based on the selection of elements displayed on the screen 230 that can be selected or activated through the orientation of the operator's gaze.

The central processing unit 200 can comprise any type of processing hardware such as a dedicated server, a PACS system of a hospital or clinic, a cloud server or a combination of distributed servers connected by means of protocols, for example peer to peer that can also operate according to blockchain-type protocols in order to validate both the programs, the acquired data and the data relating to diagnoses, as well as data relating to patients and/or medical and paramedical staff who operated on the patient.

As regards the individual units, i.e. probe 101, optional local processing unit 240, central processing unit 200, display terminal and user interface 230, augmented reality systems 250 according to the definition indicated above, these may comprise an architecture hardware that includes dedicated and non-generic hardware components, such as the electroacoustic transducer arrays of the probes and/or the interfaces with the user's body or sensory organs, such as screens, gloves, microphones, speakers, motion sensors and others. These components are summarized with box 310 in a basic diagram of an architecture according to an example embodiment of the present disclosure of said units 101, 230, 240, 250, 200 of the ultrasound system.

The functions of said dedicated hardware 310 can be comprised into the hardware itself or can be in the form of programs loaded and executed by a hardware processor that is included in each or only part of said units 101, 230, 240, 250, 200.

This processing hardware can comprise a generic standard hardware such as a PC, a workstation, a CPU or the like which executes an operating system 330 and in whose memories are loaded the programs wherein the instructions are provided for making said processing hardware 320 suitable for executing one or more of the processing steps relating to the acquisition and generation and also to the processing of ultrasound images as specified above and possibly also to the execution of the data quantity reduction steps as specified above.

According to an example embodiment of the present disclosure the programs which encode the instructions for the execution of the processing steps can each be related to a single processing step or combine several processing steps together and are realized as applications 370 intended to be included and executed in the 360 container scope. These are managed by a 340 management engine.

In the context of virtualization approaches, a container is a form of virtualized server at the operating system level. Instead of creating a virtual instance of an entire physical server (processor, storage, network connections, operating system . . . ) as happens for virtual machines, in the containerized IT approach a virtual instance is activated only of the user space, therefore essentially of the application execution environment.

Everything that supports this environment—therefore from the operating system "down" to the hardware—is not virtual but real and shared among all the running containers.

Not having to include all the resources of a server, in particular the operating system kernel, containers are much "lighter" than virtual machines, require few CPU resources and can be activated in a few moments. This makes them particularly suitable for situations wherein the processing load to be supported is highly variable over time and has unpredictable peaks.

To implement the containers an engine abstraction module 340 between the "host" operating system and the containers is required. In a Linux environment, an example of a possible solution is the Docker open source platform, supported and often included in most of the major Linux distributions.

In the Windows environment, there are two different types of Windows Containers:

Windows Server Containers: Provide a layer of isolation between applications using namespace-based technologies and process separation, but share the kernel between all containers running on the same host.

Hyper-V Containers: Execute each container in an optimized virtual machine, wherein a different kernel instance not shared with the other Hyper-V is executed.

These are only examples that are easily available on the market and of which there is also an extensive technical description, for example www.docker.com, https://kubernetes.io/it/docs/concepts/overview/what-is-kubernetes/, https://www.openshift.com/.

FIG. 3 therefore shows a basic architecture of units 101, 200, 220, 230, 240, 250 which provides for the generation of an environment for executing the programs which include the instructions for executing the various processing steps of ultrasound imaging in environments isolated and containerized, each for at least one of said programs.

According to yet another feature of containerization, this allows the execution of programs, or applications 370 independently of the hardware and operating system, thus allowing to simply transfer a container and the corresponding application and therefore the processing step in it coded from one unit to another regardless of the type of hardware provided and/or the operating system executed by it, being required only the container engine 340 on which the containerization process is based.

Thanks to this remarkable portability in a dematerialized system for ultrasound imaging, it is possible to allow a dynamic variation of the distribution of the processes described above from one unit to another, for example in the event of a limitation of the bandwidth for communication between two of these units, such as the probe and the central processing unit or this central processing unit and the display terminal and/or other combinations evident from the above described in the previous examples.

Other reasons that may require the transfer of processes from one to another of the units that make up the ultrasound system may be, for example, a reduction in the state of charge of the power supply accumulators such as the probe or other contingent and transitory reasons, therefore not systematically predictable.

FIG. 4 shows in labelled form several examples of distribution of the processing steps for the acquisition and generation of ultrasound images on the various operating units 101, 240, 200 and 230 defined above.

Although the table shows the functions, i.e. the processing steps, such a representation is only iconic and aims to simplify so as to be able to easily compare them with each other the structure of the individual operating units, i.e. probe 101, local processing unit 240, central processing unit 200, display terminal and user interface 230, 250 in relation to the processing steps.

As shown in FIG. 3, the basic architecture is substantially identical for each of the operating units of the system, the units that execute the processing steps being a computer having a conventional hardware, which execute a containerized software each of them defines the environment for the execution of one or more specific software wherein the instructions for executing each of the functions respectively assigned to one of the said operating units are coded.

It therefore appears that each of the operating units defined by the probe and optionally by a local processing unit, by a central processing unit and by a display and user interface terminal substantially differs in principle as regards the processing steps attributed to it by the fact of having loaded and executed the corresponding software.

Each box in the table is therefore to be considered as a combination of a processing hardware that executes a containerized program in which applications, having instructions coded to make the hardware capable of performing the indicated function, are executed.

With reference to FIG. 5, this very schematically shows an example of a system distributed in a hospital or other health facility. In the rooms intended to accommodate patients there is a WiFi or wireless access point according to other protocols to a communication network 220 with a centralized image generation and processing server indicated with 200 and which assumes all the typical functions of an ultrasound machine with respect to image generation from image data acquired by a probe and any processing of the same.

The server is capable of performing functions on image data acquired using three different probes on three different patients. The probes 101 transmit via wireless communication and with their univocal identification code the image data to the central unit 200. This in turn, after having generators the image, always transmits the images generated by means of the network 220 to the corresponding displays 230 and/or the results of the processing.

The action takes place in real time or with a time shift that can be considered in real time and allows the user to have the same sensations and experiences of acquiring and viewing images as with a traditional ultrasound system. Thanks to the IDs of the probes uniquely associated with a corresponding display 230, the images of each probe 101 are displayed in the closest display to them.

With 240 the local processing units are shown. These may not even be present.

According to one embodiment, these local units can each be provided for a single patient station and therefore for a single examination probe. An executive variant illustrated in the figure instead provides that the local unit 240 can be associated with two or more patient stations and therefore with two or more probes that perform two different examinations at the same time. In the upper part of FIG. 5 a local unit with a discontinuous line is shown to show the executive variant wherein one or more probes communicate directly with a central processing unit 200, this central unit being configured to perform all processing steps attributable to the local unit which is omitted, in addition to those attributed to the central unit itself.

According to another characteristic of the present ultrasound system, the probe and/or the display and user interface terminal are provided with spatial localization systems, while the central processing unit comprises a virtual map of the area wherein the probes and/or o display and/or user interface terminals and a unit for determining the position of the probes and/or display and/or user interface terminals with reference to said virtual map, which unit for determining the position automatically associates a probe to at least one display terminal as a function of the relative distance between them and the absence of obstacles which make it impossible to see the terminal directly from the position of the probe, since the terminal closest to it is associated with the probe.

According to an executive variant, the univocal association between the probe and the display terminal and/or user interface can occur directly between said probe and said terminal thanks to a direct communication of the reciprocal positions and of the reciprocal identification codes, the probe and/or said terminal by transmitting to the central unit the pairing condition to display the images generated by the data acquired by the probe on the terminal associated with it and/or to transmit user input to the probe and/or to the central processing unit.

An executive variant can provide a user interface terminal in the form of a display screen and/or in the form of one or more buttons also on the probe itself, the display screen being intended to show information on the probe produced by the probe itself and/or information transmitted by the central unit and/or by the display and/or user interface terminal and the input buttons being the ones to transmit commands and/or settings to the units integrated in the probe itself and/or to the central processing unit and/or directly to the display and/or user interface terminal associated with the probe.

According to a still further embodiment which can be provided in combination with one or more any of the previous embodiments, the ultrasound system provides a module for coding the images generated by the central unit for generating and/or processing images in the form of a file video, the central unit being provided with a streaming module for the streaming transmission of the ultrasound images to the display terminal.

According to a further feature, the central image generation and/or processing unit also provides a combination module with said ultrasound images of a graphical user interface and the coding of said combination in the form of a video signal, as well as the transmission in streaming of said video signal by means of a streaming transmission module.

Still according to an embodiment, the wireless communication network can advantageously be a network according to any protocol and technology as well as for example a virtual network with 5G architecture, as previously defined or possibly an optical fiber network.

It is worth considering here that the present disclosure is not limited to the combination with an ultrasound imaging system, but the technical teaching can also be applied to other imaging systems that provide other types of target scanning units based on the excitation of response signals from a target and the reconstruction of an image based on these response signals.

Such systems are for example MRI systems, radiological systems such as tomography and/or other similar systems.

Therefore, an example embodiment of the present disclosure can also refer to a generic imaging system for the acquisition, generation and processing of diagnostic images which system comprises:

at least one target scanning system equipped with a communication unit to transmit the corresponding data to one or more processing units also equipped with a communication unit;

a plurality of display and/or user interface terminals provided in the vicinity of the examination sites and provided with a communication unit for transmitting to and receiving data from one or more of said processing units and/or from one or more of said scanning unit;

a communication network which connects the communication units of said scanning units, of the display and user interface terminals and of said one or more processing units to each other;

said scanning units and said display and/or user interface terminals each being identified by a corresponding ID and;

said one or more processing units being designed to perform each at least part of the processing steps of the transmission and reception signals for the acquisition, generation and processing of images from said reception data, said processing units being defined by a processing hardware comprising at least one processor, at least one memory, at least one communication unit in transmission and reception, at least one input port and one output port for data and/or commands, at least one program being loaded into said processing units wherein the instructions to execute are encoded, making said processing unit or units capable of executing at least one or more processing steps for transmission and reception signals for acquisition, the generation and processing of images from said reception data;

and wherein each processing step and/or a group of two or more processing steps are in the form of containers comprising the application that contains the instructions for the execution of the processing step or steps to the processing unit and the environment execution of the application with the relative settings, that is the file system, the libraries and the API interface connections necessary for the execution of the application, a management program which defines the container engine being loaded into the processing units and being executed by them.

The invention claimed is:

1. Multi-user system for the acquisition, generation and processing of diagnostic images, which system includes:

a plurality of ultrasound probes configured to scan patients in predetermined examination sites and equipped with a communication unit to transmit the corresponding data to one or more processing units also equipped with a communication unit;

a plurality of displays and/or user interface terminals provided in the proximity of the examination sites or even in remote locations and provided with a communication unit for transmitting to and receiving data from at least one of said one or more processing units and/or from one or more of said probes;

at least one communication network which connects the communication units of the probes, displays and user interface terminals and said one or more processing units together;

said probes and said displays and/or user interface terminals each being identified by a corresponding ID;

said one or more processing units each comprising a processing hardware comprising at least one processor, at least one memory, at least one communication unit for transmission and reception, at least one input port and one output port for data and/or commands, at least being loaded into each of said one or more processing units a program in which the instructions to execute are coded to make said one or more processing units capable of performing at least one or more processing steps to carry out each at least part of the processing steps of the transmission and reception signals for the acquisition, generation and processing of images from the said received data, wherein each processing step and/or a group of two or more processing steps are in the form of containers comprising the application that contains the instructions for the execution of the processing step or steps of said one or more processing units and the environment execution of the application with the relative settings, the libraries and the application programming interface (API) interface connections necessary for the execution of the application, and a management program that constitutes a container engine for the containers is loaded in said one or more processing units and executed by said one or more processing units;

wherein the containers share a host operating system configured as a real operating system instead of a virtual operating system; and wherein the container engine is configured as an engine abstraction module operating between the containers and the real operating system to execute the said application in respective ones of the containers independently of the real operating system and the said processing hardware to allow transfer of one of said containers and the corresponding application to another of the processing units regardless of type of hardware and/or operating system employed by the another of said processing units.

2. System according to claim 1, wherein a distributed structure of said one or more processing units is provided, comprising at least two processing units chosen from said one or more processing units which are each integrated, respectively, in the probe and/or in an optional local processing unit associated with one or more patient stations and dedicated to a single probe or to a partial number of probes and possibly positioned in the immediate proximity of the said one or more patient stations and/or in a remote central processing unit which is associated with all and/or at least part of the corresponding said probe and/or said local processing unit, and/or with one or more of said plurality of display(s) and user interface terminal(s), said at least two processing units communicating between them;

and the processing steps of the reception signals of the probe or probes being divided on the said at least two processing units in such a way that one or more of the said processing units carries out only a part of the processing steps.

3. System according to claim 1, further comprising applications, each of which applications is included and executable in a corresponding container or at least two of which applications are included and executable in a corresponding container and each of which applications comprises the code for the execution of at least one of the processing steps that can be selected from the following list:

calculation of transmission timing;

generation of digital transmission signals;

D/A (digital/analogue) conversion of the transmission signals,

A/D (analogue/digital) conversion of the received signals;

beamforming in reception;

subsequent operations generically defined in the technical field as "back end processing" selected from the group:

extraction of I/Q data from the reception signals subjected to beamforming;

combination of reception data relating to temporally successive transmissions;

extraction of an envelope of the reception signals;

compression and decimation of a reception signal;

alternative processing to image generation B-mode, Doppler, CFM and other modes;

post processing activities on at least one of the images;

scan conversion;

image filtering;

image enhancement or other image optimization processing, image measurements, as well as advanced imaging modalities such as elastography, attenuation imaging and combinations thereof, zero footprint export of clinical data comprising anonymized images so as to be able to perform labelling for artificial intelligence even remotely without accessing to patient data.

4. System according to claim 2, wherein the probe(s) and/or said local processing unit and/or said central processing unit and/or the display(s) and/or user interface terminal (s) can communicate alternatively or in combination, due to a selection of the communication mode, through a cable connection and/or a wireless connection.

5. System according to claim 1, wherein at least one memory is provided for patient data corresponding to the images and at least one processing step which provides for access to patient data after authentication and authorization, while providing for the access and transmission in anonymized form without personal data of a patient or patients showed, to other processing units, such as a remote work station for a second opinion diagnosis comprising an additional diagnosis further to an onsite diagnosis.

6. System according to claim 2, comprising a local unit associated with a group of patient stations comprising two or more patient stations, a probe being provided for each station and/or for two or more patient stations of said group and alternatively or in combination being provided a central processing unit which operates in combination with one or more groups of patient stations comprising probes and/or local processing units.

7. System according to claim 1, wherein said one or more processing units are configured to perform one or more processes for reducing amount of data, such processes being selected from the following list:

Adaptive time decimation of the data, according to a predetermined bandwidth, by adjusting sampling frequency according to Nyquist limit that corresponds to twice a maximum frequency chosen from maximum frequency for RF data, and maximum frequency-minimum frequency for IQ data;

Use of a subset of receiving transducers, calculated based on a maximum receiving aperture actually used to combine signals related to a given transmission;

Under sampling, periodic or aperiodic, in time domain or in a domain of the receiving channels or in both and use of compress sensing techniques for image reconstruction based on sparse priorities in the image domain or in a transformed domain chosen from a Fourier transform, k-space, wavelet;

Under sampling, periodic or aperiodic, in the time domain or in the domain of the receiving channels or both, and use of machine learning techniques for reconstruction of missing data;

Under sampling by reducing amount of data by multiplying signals received by a matrix with a number of rows less than a number of columns;

use of advanced beamforming techniques that make it possible to obtain images of equal or similar quality compared to standard line by line isolation, reducing number of transmissions and therefore amount of data necessary to form a frame, such as those selected from the following list: multiline beamforming in reception, synthetic transmit beamforming (STB), retrospective transmit beamforming (RTB), synthetic aperture imaging, plane wave or diverging wave beamforming;

combination of beamforming based on synthetic aperture or plane wave or diverging wave beamforming, with a reduction in the number of transmissions and with a machine learning algorithm that maps the low-quality images obtained with a limited number of insonifications, on images that reproduce high-quality image characteristics that would have been obtained with a higher number of insonifications;

two-stage beamforming or micro beamforming in which part of beamforming is carried out on a probe on distinct groups of transducers, thus reducing number of communication channels between the probe and the multi-user system and consequently the data transfer rate, and in which the further part of the beamforming is carried out by a local and or central processing unit, the instructions for the execution of said processes being codified in one or more corresponding applications each or a plurality of these included and executable in a corresponding container.

8. System according to claim 2, wherein at least some probes and/or at least some central processing unit(s) and/or at least some local processing unit(s) and/or at least some display(s) and/or user interface terminal(s) comprise a processing hardware and a memory in which one or more applications are stored or can be stored in the form of containers, a measuring device for measuring of available bandwidth being provided for the connection between probes, local processing unit(s), central processing unit(s) and display(s) and user interface terminal(s) which, according to the detected communication bandwidth and a minimum threshold value or possible occupation of said band, execution of the processing steps on the probes and/or on the local processing unit(s) and/or on the central processing unit(s) and/or on the display(s) and user interface terminal(s) is distributed by enabling and disabling the execution of the corresponding applications in the corresponding containers and/or transferring one or more probes and/or one or more of the local processing unit(s) and/or one or more central processing unit(s) from one to the other/or of one or more display(s) and/or user interface terminal(s), the containers corresponding to the processing steps to be performed by the corresponding probe and/or local processing unit(s) and/or central processing unit(s) and/or display(s) and/or user interface terminal(s).

9. System according to claim 2, wherein the communication unit between the probes and/or the local processing unit(s) and/or the display(s) and user interface terminal(s) are based on an architecture of a virtual network that uses 3rd Generation Partnership Project (3GPP) standard for fifth generation wireless network.

10. System according to claim 2, wherein at least some of the display(s) and/or user interface terminal(s) comprise an interface device for augmented reality.

11. System according to claim 10, wherein the interface device for augmented reality comprises one or more of the units listed by the following list:

Surface Studio and Dial®, Azure Kinetic DK, Intel Real Sense, Speech recognition, HoloLens, gesture recognition, gaze orientation recognition or a combination of these.

12. System according to claim 2, wherein at least some probes and/or at least some central processing unit(s) and/or at least some local processing unit(s) and/or at least some display(s) and/or user interface terminal(s) comprise a processing hardware and a memory in which one or more applications are stored or can be stored in the form of containers, local processing unit(s), central processing unit(s) and display(s) and user interface terminal(s) which, as a function of available bandwidth for communication and a minimum threshold value or possible occupation of said band, execution of the processing steps on the probes and/or on the local processing unit(s) and/or on the central processing unit(s) and/or on the display(s) and user interface terminal(s) is distributed by enabling and disabling the execution of the corresponding applications in the corresponding containers and/or transferring one or more probes and/or one or more of the local processing unit(s) and/or one or more central processing unit(s) from one to the other/or of one or more display(s) and/or user interface terminal(s), the containers corresponding to the processing steps to be performed by the corresponding probe and/or local processing unit(s) and/or central processing unit(s) and/or display(s) and/or user interface terminal(s).

13. System for the acquisition, generation and processing of diagnostic images which system includes: at least one target scanning unit equipped with a communication unit to transmit the corresponding data to one or more processing unit(s) that are each also equipped with a communication unit; a plurality of displays and/or user interface terminals provided in the proximity of the examination sites and each provided with a communication unit for transmitting to and receiving data from one or more of said processing unit(s) and/or from one or more of said scanning unit; a communication network which connects the communication unit of each of the one or more said scanning unit, of the displays and user interface terminals and of said one or more processing unit(s); the one or more said scanning unit and said displays and/or user interface terminals each being identified by a corresponding ID and;

the said one or more processing unit(s) being designed to perform each at least part of the processing steps of the transmission and reception signals for the acquisition, generation and processing of images from said reception data, the said processing unit(s) comprising a processing hardware comprising at least one processor, at least one memory, at least one communication unit for transmission and reception, at least an input port and an output port for data and/or commands, said processing unit(s) being uploaded with at least one program in which the instructions to execute are encoded, making the said processing unit(s) capable of executing at least one or more processing steps for transmission and reception of signals for the acquisition, generation and processing of images from said reception data;

and in which each processing step and/or a group of two or more processing steps are in the form of containers including the application that contains the instructions for the execution of the processing step(s) of the processing unit(s) and the application execution environment with its settings comprising file system, libraries and connections of application programming interface (API) interface necessary for the execution of the application, and a management program that constitutes the container engine for the containers is loaded in the processing unit(s) and executed by processing unit(s);

wherein the containers share a host operating system configured as a real operating system instead of a virtual operating system; and wherein the container engine is configured as an engine abstraction module operating between the containers and the real operating system to execute the said application in respective ones of the containers independently of the real operating system and the said processing hardware to allow transfer of one of said containers and the corresponding application to another of said processing unit(s) regardless of type of hardware and/or operating system employed by the another of said processing units(s).

14. Multi-user system for the acquisition, generation and processing of diagnostic images, which system includes:

a plurality of ultrasound probes configured to scan patients in predetermined examination sites and equipped with a communication unit to transmit the corresponding data to one or more processing units also equipped with a communication unit;

a plurality of displays and/or user interface terminals provided in the proximity of the examination sites or even in remote locations and provided with a communication unit for transmitting to and receiving data from at least one of said one or more processing units and/or from one or more of said probes;

at least one communication network which connects the communication units of the probes, displays and user interface terminals and said one or more processing units together;

said probes and said displays and/or user interface terminals each being identified by a corresponding ID;

said one or more processing units each comprising a processing hardware comprising at least one processor, at least one memory, at least one communication unit for transmission and reception, at least one input port and one output port for data and/or commands, at least being loaded into each of said one or more processing units a program in which the instructions to execute are coded to make said one or more processing units capable of performing at least one or more processing steps to carry out each at least part of the processing steps of the transmission and reception signals for the acquisition, generation and processing of images from the said received data, wherein each processing step and/or a group of two or more processing steps are in the form of containers comprising the application that contains the instructions for the execution of the processing step or steps of said one or more processing units and the environment execution of the application with the relative settings, the libraries and the application programming interface (API) interface connections necessary for the execution of the application, and a management program that constitutes a container engine for the containers is loaded in said one or more processing units and executed by said one or more processing units;

wherein a distributed structure of the processing units is provided, comprising at least two of the said processing units which are each integrated, respectively, in the probe, said processing units being communicating between them;

and the processing steps of the reception signals of the probe or probes being divided on the said processing units in such a way that one or more of the said processing units carries out only a part of the processing steps;

wherein the containers share a host operating system configured as a real operating system instead of a virtual operating system; and wherein the container engine is configured as an engine abstraction module operating between the containers and the real operating system to execute the said application in respective ones of the containers independently of the real operating system and the said processing hardware to allow transfer of one of said containers and the corresponding application to another of the processing units regardless of type of hardware and/or operating system employed by the another of said processing units.

\* \* \* \* \*